(12) United States Patent
Tchinnis et al.

(10) Patent No.: US 6,379,682 B1
(45) Date of Patent: Apr. 30, 2002

(54) CLEAR WATER-IN-OIL EMULSIONS

(75) Inventors: Paul C. Tchinnis, Copiague; Zsolt Bagdi, Glen Cove; Peter J. Lentini, Bayside, all of NY (US)

(73) Assignee: Color Access, Inc., Melville, NY (US)

( * ) Notice: Subject to any disclaimer, the term of this patent is extended or adjusted under 35 U.S.C. 154(b) by 0 days.

(21) Appl. No.: 09/498,892

(22) Filed: Feb. 7, 2000

(51) Int. Cl.$^7$ ............................. A61K 7/00; A61K 7/48; A61K 7/32
(52) U.S. Cl. ............................ 424/401; 424/65; 424/66; 514/844; 524/588
(58) Field of Search ............................ 424/401, 65, 66; 514/844; 524/588

(56) References Cited

U.S. PATENT DOCUMENTS 5,456,906 A      10/1995   Powell et al. .................. 424/66
5,798,111 A  *   8/1998    Kanga et al. .................. 424/401
5,980,874 A  *   11/1999   Foerster et al. ................ 424/65

FOREIGN PATENT DOCUMENTS

JP      64-22344      1/1989
JP      6212108       8/1994

OTHER PUBLICATIONS

Dow Corning Corporation, No. ESA/SFA 1995, Silicone Formulation Aids Applying theTechnology—21 pages.

* cited by examiner

Primary Examiner—Diana Dudash
Assistant Examiner—Mina Haghighatian
(74) Attorney, Agent, or Firm—Karen A. Lowney, Esq.

(57) ABSTRACT

The invention relates to a cosmetic or pharmaceutical clear water-in-oil emulsion, comprising a water droplet phase dispersed in an oil phase, the average droplet size being no greater than about $1\mu$, the refractive indices of the oil and water phases being matched to within 3 parts in 10,000.

17 Claims, No Drawings

CLEAR WATER-IN-OIL EMULSIONS

FIELD OF THE INVENTION

The invention relates to cosmetic and pharmaceutical compositions. More particularly, the invention relates to water-in-oil compositions having enhanced clarity.

BACKGROUND OF THE INVENTION

In recent years, the availability of crystal clear personal care and cosmetic products has become increasingly important to the consumer. A clear product is perceived as light, clean, fresh and often cooling, features that can be important in certain types of products, for example, products for use in the sun, or makeup or skin care products to be used in warmer weather. Products of this type have largely been limited to very specific forms, however, such as gels, soap-based sticks, and thin liquids; the more traditional cosmetic vehicles, i.e., water and oil emulsions, have been less successfully converted to a clear form. Water-in-oil products are particularly desirable for certain uses, because they spread easily and evenly, forming a long-lasting, continuous, protective film on the skin, and also mimic the skin's natural lipid barrier. Such characteristics are important in products that are desirably water-proof and/or long-wearing, e.g., such as sunscreens, moisturizers, and self-tanners. The nature of the emulsion, however, in which two mutually insoluble or nearly insoluble phases are dispersed one within the other, does not easily achieve clarity because of the discontinuous droplet phase dispersed within the continuous phase: opacity typically results due to the refraction and reflection at the emulsion interface, as light is transmitted through the continuous phase and into the dispersed phase.

Transparent emulsions can be prepared in the form of microemulsions, in which the dispersed phase is essentially solubilized in the continuous phase by the action of a surfactant, and often, a cosurfactant. Rather than discrete isolated dispersed phase droplets, micelles comprising an inner core of the disperse phase material surrounded by a layer of surfactant are formed. These systems upon formation are normally clear, forming very small micellar droplets, but ordinarily require fairly large quantities of surfactant. Normally, it is desirable to keep surfactant levels low in cosmetic compositions, however, because they can strip the skin of its natural lipid barrier, and thus leave the skin more susceptible to irritants.

Alternate efforts to resolve this problem have turned to matching of refractive indices between the components of the two phases. Water and most water-soluble materials have a relatively low refractive index, i.e., about 1.3–1.4, whereas oils and oil soluble materials have refractive indices that range from about 1.4–1.5 for silicone oils, up to about 1.5–1.6 for hydrocarbons. In order to match the two phases, it is necessary to add a further component to the mix to either adjust the water phase index up, or reduce the oil phase index. Most frequently, the additional component is a glycol, usually in fairly high percentages, added to the water phase. Although the resulting product will appear to be clear, it is normally undesirable to use high levels of glycols in cosmetic products, since these compounds are themselves often irritating to the skin of the user. Additionally, since the amount of water that can stably be incorporated into a water-in-oil emulsion is limited, the use of large quantities of glycols in the aqueous phase necessarily reduces the amount of water, and the amount of water soluble actives, that can be used in the emulsion.

There continues to be a need for a clear water-in-oil emulsion that permits reduction in the amount of irritating surfactants and glycols, and in which the amount of water and water-soluble actives can be correspondingly increased.

SUMMARY OF THE INVENTION

The present invention relates to cosmetic and pharmaceutical clear water-in-oil emulsions, comprising a water droplet phase dispersed in an oil phase, the average droplet size less than about $1\mu$, the refractive indices of the oil and water phases being matched to within 3 parts in 10,000. In a preferred embodiment, the composition comprises less than about 15% by weight of a glycol, and also comprises no more than 1.5% of a surfactant. Preferably the composition contains at least about 30% of water.

The invention also relates to a method for making a clear water-in-oil emulsion comprising adjusting the refractive indices of the oil and water phases to within 3 parts in 10,000, employing no more than about 15% of a glycol, and emulsifying the phases under high shear to obtain an average dispersed water droplet size of less than about $1\mu$.

DETAILED DESCRIPTION OF THE INVENTION

The compositions of the invention are true water-in-oil emulsions, rather than microemulsions, with exceptional clarity, a trait previously difficult to achieve in a true emulsion without the use of substantial quantities of irritating substances such as glycols and surfactants. The clarity of the emulsion is obtained by the control of two different aspects of the composition. The first aspect is matching the refractive indices of the oil and water phases. In the present case, the refractive index of the water phase is adjusted by the addition of an a water-soluble material other than a glycol. By "glycol" in the context of the present specification and claims is meant a $C_{2-4}$ diol such as ethylene, butylene or propylene glycol. In a preferred embodiment, the added compound used for adjustment is a glycerin polymer. The polymer can contain from 2–60 glycerin subunits; preferably, the polymer contains from 2–10 glycerin subunits, and most preferably contains from 2–5 glycerin subunits. Examples of useful polymers include diglycerol, triglycerol, oligoglycerols, and polyglycerols, or a combinations thereof. Particularly preferred is diglycerol.

The amount of glycerin polymer to be added to the aqueous phase will vary depending upon the refractive index of the oil phase to be matched. The refractive index of the water phase and the oil phase should be matched to within 0.0003 refractive index units. The absolute value of the refractive index is not critical, provided that both are matched to within the specified limits or better. It is possible to create a clear emulsion using any oil, or oil-soluble material, as a component of the oil phase. The major oil component can be either hydrocarbon, silicone-based oils, oily esters or any combination of these. Examples of oils useful in the invention include, but are not limited to, vegetable oils, such as coconut oil, jojoba oil, corn oil, olive oil, sunflower oil, palm oil, and soybean oil; carboxylic acid esters such as isostearyl neopentanoate, cetyl octanoate, cetyl ricinoleate, octyl palmitate, dioctyl malate, Icoco-dicaprylate/caprate, decyl isostearate, myristyl myristate; animal oils such as lanolin and lanolin derivatives, tallow, mink oil or cholesterol; glyceryl esters, such as glyceryl stearate, glyceryl dioleate, glyceryl distearate, glyceryl linoleate, glyceryl myristate; nonvolatile hydrocarbons, such as isoparaffins, squalane, or petrolatum; and volatile hydrocarbons, such as straight or branched chain hydrocarbons having from 8–20 carbon atoms, e.g., decane, dodecane, tridecane, tetradecane, and C8–20 isoparaffins. However, because of the refractive index of silicone oils is closer to that of water, it is often preferred to use one or more silicone oils as the principle oil component. The silicone oil can be selected from volatile silicones, such as the cyclic (cyclomethicone) or linear (dimethicone) polydimethylsiloxanes, having from three to nine carbon atoms. The silicone oil may also be a nonvolatile oil, such as higher molecular weight dimethicones, dimethiconol, phenyl trimethicone, methicone, or simethicone. Typically, the oil component will comprise from about 10 to about 50%, preferably about 20 to about 30%, by weight of the composition as a whole, and the water component from about 30 to about 90 %, preferably about 50 to about 90%, most preferably about 70–80%. As noted above, the amount of refractive index-adjusting component employed in the water phase will vary depending on the identity of the oil to be matched, as well as the other components to be included in the composition; however, the amount will ordinarily be in the range of about 0.01 to about 10%, preferably about 0.5 to about 5%.

The composition of the invention is unusual in its use of relatively small amounts of glycols. While some glycols may be used in the water phase to assist in matching refractive indices, preferably no more than about 15%, more preferably no more than about 5%, of standard glycols are employed. If used, the glycol is preferably selected from the group consisting of butylene glycol, propylene glycol, ethylene glycol and trimethylene glycol, dipropylene glycol, isoprene glycols and polyethylene glycols. Because of the refractive index adjustment can be achieved with the use of relatively low levels of glycols and glycerin polymers, it is possible for the composition to contain up to 90% water and water-soluble actives, exclusive of glycols and glycerin polymers.

The composition also achieves a clear water-in-oil emulsion without the formation of a microemulsion, and consequently, with the use of very little surfactant. When used, the amount of surfactant is ordinarily less than about 3%, preferably less than about 1.5%. The preferred surfactant for use in the composition is a low HLB (i.e., no higher than 5) surfactant, examples of which can readily be obtained in McCutcheon's Emulsifiers and Detergents, North American Edition, 2000.

In addition to the actual components of the composition, the processing of the composition is important in achieving a superior clarity. It is desirable to achieve a water phase average droplet size of less than $1\mu$, preferably in the range of from about 100 to about 900 nm. This is typically achieved by processing the components in a high shear homogenizer, which will reduce droplet size beyond the size capable of being obtained with standard mechanical mixing. Examples of appropriate homogenizers are Silverson homogenizers (L4RT-A; Silverson Machines, Ltd., Chesham, England) and Greerco homogenizers(IL; Baldor Electric Co., Ft. Smith, AK.). Processing speeds in excess of 3000 rpm are generally needed in order to achieve the preferred droplet size. The process should be preferably conducted without heat, more preferably at room temperature. In order to facilitate obtaining the desired small size droplet, and a stable product, it is preferable to utilize a low HLB emulsifier. The preferred emulsifier has an HLB value of no greater than 6,preferably from about 2 to about 4 and preferably also has a low refractive index. Suitable water-in-oil emulsifiers include, but are not limited to, sorbitan derivatives such as sorbitan laurate and sorbitan palmitate; alkoxylated alcohols such as laureth-4; hydroxylated derivatives of polymeric silicones, such as dimethicone copolyol; alkylated derivatives of hydroxylated polymeric silicones, such as cetyl dimethicone copolyol; glyceryl esters such as polyglyceryl-4 isostearate; beeswax derivatives such as sodium isostearoyl-2-lactylate; lecithin; and mixtures thereof. In conjunction with the preferred oil component being a silicone oil, the preferred emulsifiers are hydroxylated derivatives of polymeric silicones and alkylated derivatives thereof. Particularly preferred is dimethicone copolyol.

The compositions of the invention exhibit exceptional clarity, preferably with an optical clarity of less than 100 NTU, more preferably with a clarity of 50 NTU or less, can be used as a vehicle for a variety of purposes, in fact, for any type of product, either cosmetic or pharmaceutical, in which a water-in-oil vehicle is appropriate. In this regard, the basic components of the clear emulsion, as described above, will frequently be combined with other cosmetic and pharmaceutical components. Examples of such components include, but are not limited to antioxidants, antimicrobials, sunscreens, analgesics, anesthetics, anti-acne agents, anti-dandruff agents, antidermatitis agents, antipruritic agents, anti-inflammatory agents, antihyperkeratolytic agents, anti-dry skin agents, antiperspirants, antipsoriatic agents, antiseborrheic agents, hair conditioners and hair treatment agents, antiaging agents, antiwrinkle agents, antihistamine agents, skin lightening agents, depigmenting agents, wound-healing agents, vitamins, corticosteroids, self-tanning agents, or hormones. The composition can also include any one or more of strictly cosmetic ingredients, such as pigments, dyes, emollients, humectants, stabilizers, and fragrances and can be employed in various types of cosmetic products, such as bath preparations, hair conditioners, cleansers, makeup removers, and the like.

EXAMPLES

Example 1

This Example Illustrates The Method of Making a Water-in-oil Emulsion of the Invention.

A proposed formula for the product to be made is designed. The intended components of the oil phase are combined, and the refractive index measured on a Leica refractometer (Buffalo, N.Y.). The obtained "n" serves as the target value for the water phase. The water phase components are combined, but a part of the deionized water is withheld; deionized water has a refractive index of about 1.33, the lowest of all materials used in the formula. The refractive index is measured, and if the "n" value is lower than the "n" of the oil phase, the water phase is redesigned or reweighed, withholding an even larger amount of deionized water. At this point, the water phase's refractive index should be higher than that of the oil phase, for ease of future adjustment. All measurements should be done at room temperature.

While the water phase components are being mixed constantly at room temperature, small amounts of deionized water are being added to it. The amount of water added each time is determined by the difference between the "n's" of the oil phase and the water phase. At each addition, the exact amount of deionized water added is recorded, and after each addition, enough time is allowed for complete mixing. Once the mixing is complete, the refractive index is measured. The amount of decrease in the value of "n" is determined and evaluated, and used to determine the amount of additional deionized water to be added. These steps can be repeated until the refractive index of the water phase is matched to within ±0.0003. As the value of "n" for the water phase approaches that of the oil phase, the amount of deionized water being added should be decreased, to avoid missing the target by adding too much. When the refractive indices of the two phases are at the target value, within the allowed error, the total amount of deionized water in the formulation is calculated, and the matching process is complete.

The final water to oil phase ration is decided after several batches are made. The formula cannot contain any waxes, gums or thickeners that are not clear, so the viscosity is dependent on the water to oil ratio. In a water in oil system, a higher water phase percentage will yield a product with higher viscosity. Once the ratio is decided, the appropriate amounts of oil phase and water phase can be weighed out. The final formula is adjusted to reflect the new percentages of the water phase due to the adjusted deionized water level.

Once the phases are matched and final percentages and ratios determined, they are emulsified. Emulsification is conducted by a cold process, i.e., without heat, at room temperature. The oil phase is placed in the main beaker and mixed with a propeller that provides high shear mixing with no aeration (Caframo Stirrer, Warton, Toronto, Canada) Transfer rate of water into the oil is slow, taking from 45–60 minutes. The resulting average water droplet size in the emulsion is less than 200 nm. The final viscosity of the emulsion is achieved by placing the product under a Silverson homogenizer.

Example 2

The following is a formulation for a self-tanning composition prepared in accordance with the present invention.

| Material | Weight Percent |
|---|---|
| A. Oil Phase | |
| Cyclomethicone | 8.00 |
| dicaprylyl ether | 4.00 |
| isononyl isononanoate | 2.00 |
| Cyclomethicone/dimethicone/ vinyldimethicone crosspolymer | 8.00 |
| Fragrance | 0.30 |
| cyclomethicone/dimethicone copolyol | 10.00 |
| B Water Phase | |
| Deionized water | QS |
| diglycerol | 6.00 |
| ethoxydiglycol | 5.50 |
| 1,3-butylene glycol | 6.50 |
| sodium chloride | 2.00 |
| sucrose | 4.00 |
| dihydroxyacetone | 5.00 |
| glycereth-5 lactate | 6.00 |

What we claim is:

1. A cosmetic or pharmaceutical clear water-in-oil emulsion, comprising a water droplet phase dispersed in an oil phase, the average droplet size being no greater than about 1μ, the refractive indices of the oil and water phases being matched to within 3 parts in 10,000, the emulsion containing less than about 15 weight percent of glycol, and no more than 3% surfactant.

2. The emulsion of claim 1 in which the water phase comprises at least one glycerin polymer.

3. The emulsion of claim 2 in which the glycerin polymer is selected from the group consisting of diglycerol, triglycerol, oligoglycerols, and polyglycerols.

4. The emulsion of claim 3 which comprises diglycerol.

5. The emulsion of claim 1 in which the oil phase comprises a silicone oil.

6. The emulsion of claim 5 in which the silicone oil is cyclomethicone.

7. A cosmetic or pharmaceutical clear water-in-oil emulsion comprising a water droplet phase in an amount of about 30 to about 90%, dispersed in an oil phase in an amount of about 10 to about 30%, the average droplet size being no greater than about 1μ, the refracuve indices of the oil and water phases being matched to within 3 parts in 10,000, the emulsion also comprising a glycerin polymer, less than about 15 weight percent of glycol, and no more than 3% surfactant.

8. The emulsion of claim 7 in which the glycerin polymer is selected from the group consisting of diglycerol, triglycerol, oligoglycerols, and polyglycerols.

9. The emulsion of claim 7 in which the oil phase comprises a silicone oil.

10. The emulsion of claim 9 in which the silicone oil is cyclomethicone.

11. The emulsion of claim 7 which also comprises an emulsifier with an HLB of no more than 6".

12. The emulsion of claim 9 which comprises an emulsifier selected from the group consisting of hydroxylated derivatives of polymeric silicones and alkylated derivatives thereof.

13. The emulsion of claim 12 in which the emulsifier is dimethicone copolyol.

14. The emulsion of claim 7 which comprises at least about 40% of water and water soluble components, exclusive of glycols and glycerin polymers.

15. A method for making a clear water-in-oil emulsion, the emulsion comprising a water droplet phase dispersed in an oil phase, the method comprising adjusting the refractive indices of the oil and water phases to within 3 parts in 10,000, employing no more than about 15% of a glycol in the water phase, and emulsifying the phases under high shear conditions to obtain an average dispersed water droplet size of less than about 1μ.

16. The method of claim 15 in which the droplet size is between about 100 to about 900 nm.

17. The method of claim 15 which is conducted at room temperature.

* * * * *